United States Patent
Lewis et al.

(10) Patent No.: US 12,247,245 B2
(45) Date of Patent: Mar. 11, 2025

(54) SELECTIVITY SCREENING FOR ANTIMICROBIAL COMPOUNDS

(71) Applicant: NORTHEASTERN UNIVERSITY, Boston, MA (US)

(72) Inventors: Kim Lewis, Newton, MA (US); Anthony D'Onofrio, Northborough, MA (US); Thomas Curtis, Boston, MA (US); Charlotte Berkes, Melrose, MA (US)

(73) Assignee: Northeastern University, Boston, MA (US)

( * ) Notice: Subject to any disclaimer, the term of this patent is extended or adjusted under 35 U.S.C. 154(b) by 923 days.

(21) Appl. No.: 17/262,031

(22) PCT Filed: May 24, 2019

(86) PCT No.: PCT/US2019/033885
§ 371 (c)(1),
(2) Date: Jan. 21, 2021

(87) PCT Pub. No.: WO2020/023106
PCT Pub. Date: Jan. 30, 2020

(65) Prior Publication Data
US 2021/0301316 A1  Sep. 30, 2021

Related U.S. Application Data

(60) Provisional application No. 62/703,139, filed on Jul. 25, 2018.

(51) Int. Cl.
*C12Q 1/18* (2006.01)

(52) U.S. Cl.
CPC ..................... *C12Q 1/18* (2013.01)

(58) Field of Classification Search
CPC ................. C12Q 1/18; A61P 31/10
See application file for complete search history.

(56) References Cited

U.S. PATENT DOCUMENTS

| | | |
|---|---|---|
| 5,783,431 A | 7/1998 | Peterson et al. |
| 6,303,115 B1 | 10/2001 | Natsoulis |
| 2011/0171125 A1 | 7/2011 | Elkins et al. |
| 2013/0164221 A1 | 6/2013 | Cirillo et al. |
| 2015/0337351 A1 | 11/2015 | Metzger |

FOREIGN PATENT DOCUMENTS

| | | |
|---|---|---|
| EP | 3321352 A1 | 5/2018 |
| WO | 2004064732 | 8/2004 |
| WO | WO 2005/021775 A2 | 3/2005 |

OTHER PUBLICATIONS

Schellenberg et al., Journal of Microbiological Methods vol. 65, Issue 1, Apr. 2006, pp. 1-9. (Year: 2006).*
Forster et al., Applied and Environmental Microbiology, Oct. 2002, vol. 68, No. 10, p. 4772-4779. (Year: 2002).*
Hua et al., BMC Biotechnology, 2017, vol. 17, No. 5, p. 1-12. (Year: 2017).*
Fazii et al., Eur J Clin Microbiol Infect Dis, 2002, vol. 21, p. 373-378. (Year: 2002).*
Malone et al., Journal of Microbiological Methods, 2009, vol. 77, p. 251-260. (Year: 2009).*
Cormack et al., Microbiology, 1997, vol. 143, p. 303-311. (Year: 1997).*
Correa-Martinez et al. "Rapid Detection of Extended-Spectrum beta-Lactamases (ESBL) and AmpC bata-actamases in Enterobacterales: Development of a Screening Panel Using the MALDI-TOF MS-Based Direct-on-Target Microdroplet Growth Assay," Frontiers in Microbiology, 2019, vol. 10, article 13, pp. 1-7.
International Search Report and Written Opinion for International Application No. PCT /US2019/033885, dated Aug. 29, 2019, 10 pages.
European Search Repoort, Patent Application No. PCT/US2019/033885, dated May 18, 2022, 9 pages.

* cited by examiner

*Primary Examiner* — Kade Ariani

(57) ABSTRACT

Assays for compounds having a desired biological activity against one but not both of a pair of microorganism species utilize separately detectable labels. The first and second microorganisms are different from each other, the first microorganisms exhibit a first detectable label, the second microorganisms exhibit a second detectable label different from the first detectable label, and neither of the labels interferes with detection of the other label. In various embodiments, the first and second microorganisms are incubated with a candidate compound or a producer thereof. The different labels permit isolation of microorganisms exhibiting one of the labels but not the other, indicating the desired activity, and the compound responsible for this differential response is isolated.

20 Claims, 5 Drawing Sheets

SOIL SAMPLE

LOW YFP / HIGH mCherry BEADS

RANDOMLY SORTED BEAD CONTROL

PAENIBACILLUS POLYMYXA

LOW YFP / HIGH mCherry BEADS

RANDOMLY SORTED BEAD CONTROL

SELECTIVITY SCREENING FOR ANTIMICROBIAL COMPOUNDS

CROSS-REFERENCE TO RELATED APPLICATION

This application is a U.S. National Phase Application of PCT/US2019/033885, filed on May 24, 2019, which claims priority to, and the benefit of U.S. Provisional Patent Application No. 62/703,139, which was filed on Jul. 25, 2018. The foregoing applications are hereby incorporated by reference in their entireties.

GOVERNMENT FUNDING

This invention was made with government support under Grant No. P01AI118687 awarded by the National Institutes of Health. The U.S. Government has certain rights in the invention.

FIELD OF THE INVENTION

The invention relates, generally, to screening bacteria and other microbes for activity that is selective to a target microorganism or mammalian cell.

BACKGROUND

The ability to rapidly assess candidate compounds for a desired biological activity is critical to research in many areas of biomedicine, agriculture, and environmental management. While it is simple to screen individual compounds serially, it is also time-consuming, and researchers seeking to discover and isolate, for example, new antimicrobial compounds generally use in vitro plating techniques that can screen many compounds at once. Antimicrobial susceptibility testing can be used for drug discovery, epidemiology, and prediction of therapeutic outcome. Plants, soil, and other natural sources can provide a broad range of structurally diverse candidate compounds.

In agar disk-diffusion screening methods, for example, agar plates are inoculated with the microorganism against which activity is sought. Filter paper disks each containing a different test compound are placed on the agar surface, and the plates are incubated under suitable conditions. Compounds with the desired activity diffuse into the agar and inhibit germination and growth of the test microorganism. The diameters of inhibition growth zones around the disks indicate the effectiveness of the associated compounds.

One limitation of conventional methods is that, while multiple candidate compounds can be assessed simultaneously, the assay can only reveal toxicity to one target microorganism. Another limitation is that the assay will not reveal toxicity to a potential recipient of an identified compound. Assessing the latter generally requires a separate set of tests, with associated time and costs. These limitations contribute to the high cost of drug discovery.

SUMMARY

Embodiments of the present invention transform multiple microorganisms of interest so that, while alive, they exhibit independently detectable labels. (The term "microorganism" is herein used broadly to connote single-celled organisms such as bacteria as well as individual cells of a larger organism, such as mammalian cells and fungal cells.) This permits detection of differential activity against one microorganism but not another. Activity against a Gram negative organism but not a Gram positive organism allows isolation of compounds or antibiotic producers with selective activity. This is advantageous, since such detection eliminates the large background of known and generally toxic compounds. In addition, such compounds likely hit a target present in only a particular group of microorganisms, which means that humans lack this target; thus various approaches provided herein may advantageously increase the probability of discovering non-toxic compounds.

Similarly, a compound active against the fungus *Candida albicans* but not Gram-positive bacteria may prove useful as a selective, non-toxic antifungal agent. Embodiments of the present invention may be used to identify compounds with differential activity against other microorganism pairs having different biomedical significance. For example, the therapeutic target may be a mammalian cell, and the other microorganism (the "indicator" species) may be a bacterial or fungal cell, enabling identification of compounds acting selectively against cancer, inflammation or apoptosis, for example.

Assays in accordance herewith may involve candidate compounds or "producer" species, such as bacteria, that make compounds exhibiting desirable biological activity. Accordingly, in one aspect, the invention pertains to a method of detecting selective activity of a compound against microorganisms. In various embodiments, the method involves suspending first and second microorganisms in a nutrient medium, where the first and second microorganisms are different from each other, the first microorganisms exhibit a first detectable label, the second microorganisms exhibit a second detectable label different from the first detectable label, and neither of the labels interferes with detection of the other label. The method further involves contacting the first and second microorganisms with the compound or a producer thereof, isolating a volume of the nutrient medium exhibiting the first label but not the second label, and identifying the compound or producer thereof.

Accordingly, in a first aspect, the invention pertains to a method of detecting selective activity of a compound against microorganisms. In various embodiments, the method comprises the steps of suspending first and second microorganisms in a nutrient medium, wherein (i) the first and second microorganisms are different from each other, (ii) the first microorganisms exhibit a first detectable label, (iii) the second microorganisms exhibit a second detectable label different from the first detectable label, and (iv) neither of the labels interferes with detection of the other label; contacting the first and second microorganisms with the compound or a producer thereof, isolating a volume of the nutrient medium exhibiting the first label but not the second label; and identifying the compound or producer thereof.

In various embodiments, the first and second detectable labels have fluorescent emissions having different peak wavelengths. For example, the first and second microorganisms may be genetically modified to express fluorescent proteins, the peak wavelengths of which may be in the visible spectrum (e.g., one of the wavelengths is green and the other is red).

The first microorganism may be gram positive and the second microorganism may be gram negative. The first microorganism may be gram positive and the second microorganism may be a spirochete or a fungus. The first microorganism may be found in human gut flora and the second microorganism may be a disease-causing pathogen. The first microorganism may be found as a natural inhabitant of the human nasopharynx and the second microorganism may be a disease-causing pathogen. The first microorganism may be found as a natural inhabitant of the human oral cavity and the second microorganism may be a disease-causing pathogen. The first microorganism may be found as a natural inhabitant of the human vaginal microbiota and the second microorganism may be a disease-causing pathogen. The first microorganism may be found as a natural inhabitant of the human skin microbiome and the second microorganism may be a disease-causing pathogen. The first microorganism may be a bacterial or fungal cell and the second microorganism may be a mammalian cell.

In various embodiments, the selectively contacting and isolating steps comprise mixing the compound or producer thereof with agar to produce a first mixture and spreading the mixture over a plate; spreading a second mixture comprising the first and second microorganisms over the first mixture; detecting at least one region of the plate where the first label is present and the second label is not present; and isolating the compound or producer thereof from the at least one detected region. For example, the compound or producer thereof may be in a soil sample.

In some embodiments, the selectively contacting and isolating steps comprise mixing the compound or producer thereof with liquid agarose to produce a mixture and adding the first and second microorganisms to the mixture; generating microdroplets from the mixture; identifying microdroplets exhibiting the first label but not the second label; and isolating the compound or producer thereof from the isolated microdroplets. The microdroplets may include approximately equal numbers of the first and second microorganisms. The first and second detectable labels may produce fluorescent emissions having different peak wavelengths and the identifying step may be performed using a fluorescence-activated cell sorter.

In various embodiments, the contacting and isolating steps include mixing the compound or producer thereof with agarose beads and a mixture comprising the first and second microorganisms; identifying the agarose beads using forward and side scatter gating; sorting agarose beads exhibiting the first label but not the second label; and isolating the compound or producer thereof from the identified agarose beads. For example, the compound or producer thereof may be in a soil sample.

In general, as used herein, the term "substantially" means ±10%, and in some embodiments, ±5%. In addition, reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Embodiments of the present invention can screen bacteria and other microbes directly from soil and other environmental sources for activity that is selective to a target microorganism, at least with respect to a second microorganism. A target organism may be combined with an indicator species to detect selectivity of action and therefore lack of general toxicity. Each target or indicator species has a detectable label, and the labels are both independently detectable and non-interfering—i.e., it is possible to detect the presence of both labels, either label, or no label. Exposing a target and an indicator cell simultaneously to a candidate compound or a potential producing microorganism facilitates identification of activity against the target but not the indicator. Assays in accordance herewith can be carried out on solid media or using microfluidic droplets, increasing the throughput of natural product screening substantially.

In one embodiment, the label is a fluorescent protein; for example, the target and indicator species may be modified to express fluorescent proteins with different emission peaks, e.g., at green and red wavelengths. In one example, the gene for green fluorescent protein under the control of a constitutive promoter is transformed into *E. coli* by electroporation and integrates in the chromosome targeted by homologous flanking regions. Similarly, the gene for red fluorescent protein is cloned into *S. aureus*.

Various target, indicator microorganism pairs may be used depending on the objective. Representative examples include a Gram-negative target (e.g., a pathogen such as *Escherichia coli*) and a Gram-positive indicator; a spirochete and a Gram-positive indicator; or a fungus and a Gram-positive indicator. More generally, the indicator may be found as a natural inhabitant of the gut, the human nasopharynx, the human oral cavity, or the human skin (or other) microbiome, and the target microorganism may be a disease-causing pathogen. Alternatively, the indicator may be a bacterial or fungal cell and the target microorganism may be a mammalian cell, enabling identification of compounds acting selectively against cancer, inflammation or apoptosis.

In a representative implementation, the objective is to identify producing microorganisms that make compounds selectively acting against Gram-negative bacteria. *E. coli*, or a different Gram-negative pathogen, is modified through recombinant DNA techniques to express a green fluorescent protein. The gene encoding the green fluorescent protein can be transformed into the cell and either expressed on a plasmid or integrated into the chromosome. *Staphylococcus aureus*, or any other suitable Gram-positive bacterial species, is modified to express red fluorescent protein using similar techniques. These colors can be changed as desired so long as each label is independently detectable.

Figure 1:
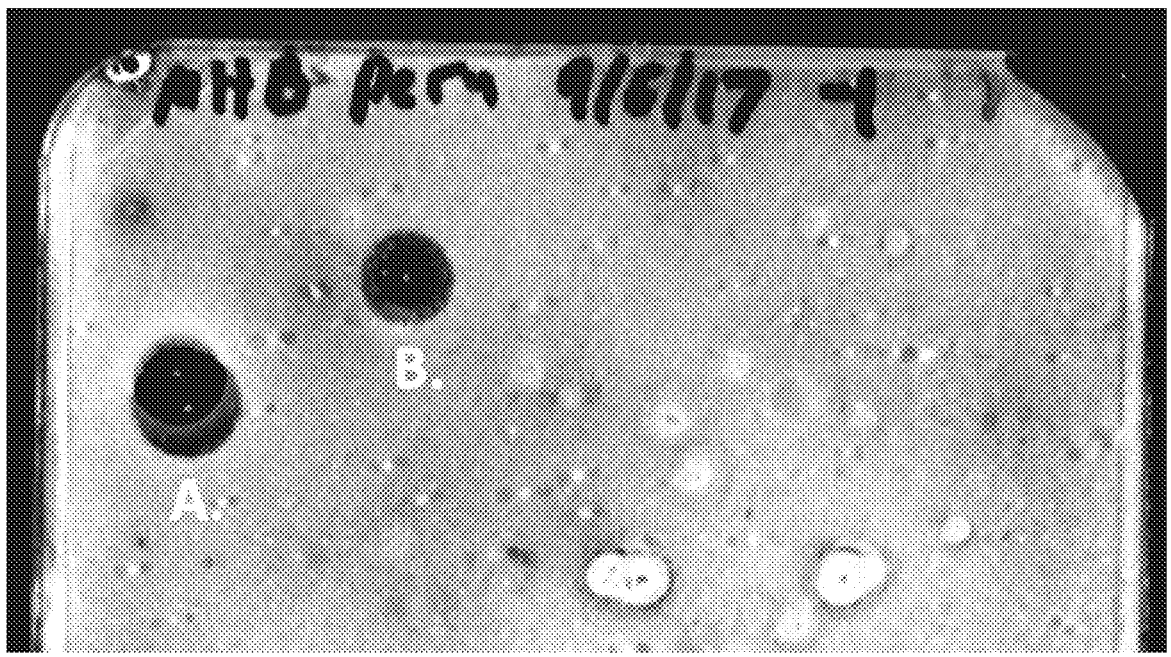
FIG. 1 illustrates the results of a plating technique in accordance with the present invention.

FIG. 1 illustrates one embodiment of the invention using a plating technique and an environmental sample, such as soil, that contains millions of cells of potential producer bacteria. In a representative procedure, the soil sample is serially diluted by creating tenfold serial dilutions in water or growth media. These are mixed with agar and poured into a large Petri plate. After incubation for 1-7 days, a diluted mixed culture of Gram-negative (e.g., *E. coli*) and Gram-positive (e.g., *S. aureus*) microorganisms, recombinantly engineered to express fluorescent proteins emitting at different wavelengths, is spread with sterile bacterial spreaders or glass beads evenly over the agar surface. After a 24-hour incubation, plates are imaged with the use of an instrument, such as a ChemiDoc Imaging System or an integrated instrumentation package such as the PHENOBOOTH supplied by Singer Instruments, that excites at wavelengths appropriate to the fluorescent proteins and records images through colored filters. Multiple images are produced using excitation and filters corresponding to each fluorescent protein wavelength, and these are then overlaid to produce a composite image. The pattern produced in the composite image reveals inhibition zones; the ones of interest reflect activity favoring growth of *S. aureus* and inhibition of *E. coli*. Colonies resulting in such inhibition zones are then isolated in by picking colonies with a fine tipped loop and re-streaking on sterile plates multiple times to isolate the producer in pure culture. The newly isolated producer is then fermented to confirm activity and isolate the antimicrobial compound.

FIG. 1 shows results from the plating iteration of this method, where an environmental sample of bacteria is suspended in agar and incubated with an overlay of green fluorescent *E. coli* and red fluorescent *S. aureus* reporter strains. In the figure, Example A shows two adjacent colonies from environmental bacterial isolates, one of which produces a *S. aureus* selective inhibition zone (halo surrounding the upper feature), while the other produces an *E. coli* selective inhibition zone (lower feature), as well as a broad-spectrum zone of activity (middle feature) where the two selective inhibition zones overlap. Example B shows a colony of an environmental bacterial isolate producing both broad spectrum (central zone) and *E. coli* selective zones (peripheral zone) of inhibition.

Figure 2:
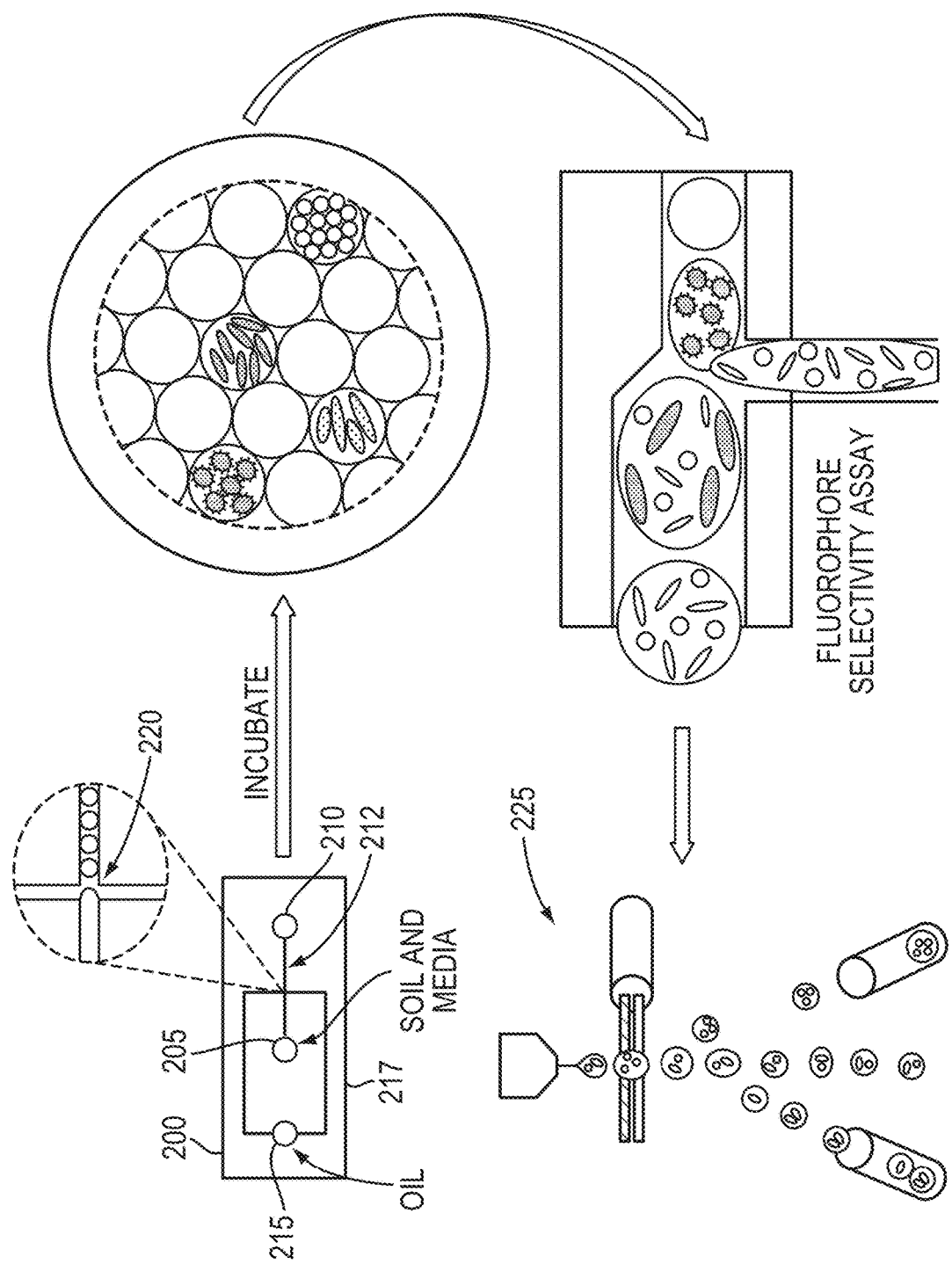
FIG. 2 illustrates a microdroplet technique in accordance with the present invention.

In another embodiment, shown in FIG. 2, the candidate compound or environmental sample (e.g., soil) is combined with the target and indicator microorganisms in liquid agarose. Cells are mixed together in such proportion to contain, on average, one cell of a producing microorganism and 10 cells each of the target and indicator microorganisms. The mixture is loaded into a first reservoir 205 of a microfluidic instrument 200. The reservoir 205 communicates with a collection reservoir 210 via a first microfluidic channel 212, through which the contents of the reservoir 205 are pumped. A fluorinated oil or other biocompatible oil is loaded into a second reservoir 215, and the oil is pumped through both branches of a second channel 217 that converges with the channel 212 at a junction 220. The junction 220 is sized and shaped, in a conventional fashion, so that the converging flow creates liquid agarose-containing microdroplets formed and suspended in the oil, collecting in the reservoir 210. In some embodiments, potential producer cells are pre-incubated in droplets before merging with a second droplet containing the fluorescent target and indicator microorganisms.

The droplets are subjected to a fluorophore selectivity assay to segregate droplets that exhibit a minimum degree of fluorescence, and these are incubated and sorted by flow cytometry. In particular, a fluorescence-activated cell sorter (FACS) 225, such as the BD FACSAria III is used to sort out and isolate droplets that exhibit the desired pattern of expression with a high ratio of, e.g., red fluorescent to green fluorescent expression. Potential producers identified in the screen are confirmed by fermenting cultures, lyophilizing, resuspending in DMSO and testing for activity. Active extracts are then fractionated by HPLC and identified through MS and NMR analysis (Ling, L. L., T. Schneider, A. J. Peoples, A. L. Spoering, I. Engels, B. P. Conlon, A. Mueller, T. F. Schaberle, D. E. Hughes, S. Epstein, M. Jones, L. Lazarides, V. A. Steadman, D. R. Cohen, C. R. Felix, K. A. Fetterman, W. P. Millett, A. G. Nitti, A. M. Zullo, C. Chen & K. Lewis, "A new antibiotic kills pathogens without detectable resistance," *Nature* 517: 455-459 (2015))

This method can be similarly used to discover compounds acting selectively against fungi such as *Candida albicans*. In this case, the indicator cells are fluorescently labeled *S. aureus* and the target cells are fluorescently labeled *C. albicans* expressing a fluorescent protein emitting at a different wavelength. In a representative procedure based on that described above in connection with FIG. 1, soil or another type of environmental sample containing potential producer microorganisms is serially diluted, mixed with agar, plated on a large petri plate and incubated at the desired temperature and length of time to allow for growth of potential producer microorganisms. After an incubation period, mixed cultures of indicator cells, such as *S. aureus* recombinantly engineered to express fluorescent proteins (e.g. mCherry) and target cells (*C. albicans* engineered to express another non-interfering fluorescent protein (e.g. GFP) are spread over the surface of the potential producer culture, incubated for 24 hours, and imaged. In this example, a colony producing an antifungal lacking toxicity against the indicator species will be surrounded by a zone in which mCherry signal is present and GFP signal is inhibited. Putative antifungal producer microorganisms giving rise to such zones are then isolated and fermented to confirm activity and isolate the antifungal compound.

Figure 3:
FIG. 3 illustrates representative results from an antifungal producer screen.

FIG. 3 illustrates representative results from an antifungal producer screen, where a dilute soil sample is suspended in agar and incubated with an overlay of green fluorescent *C. albicans* and red fluorescent *S. aureus* reporter strains. Example A" shows an environmental isolate that produces a compound with broad toxicity, inhibiting growth of both *C. albicans* and *S. aureus* (peripheral zone). Example B" shows two adjacent colonies producing a *C. albicans*-selective inhibition zone (halos).

Figure 4A:
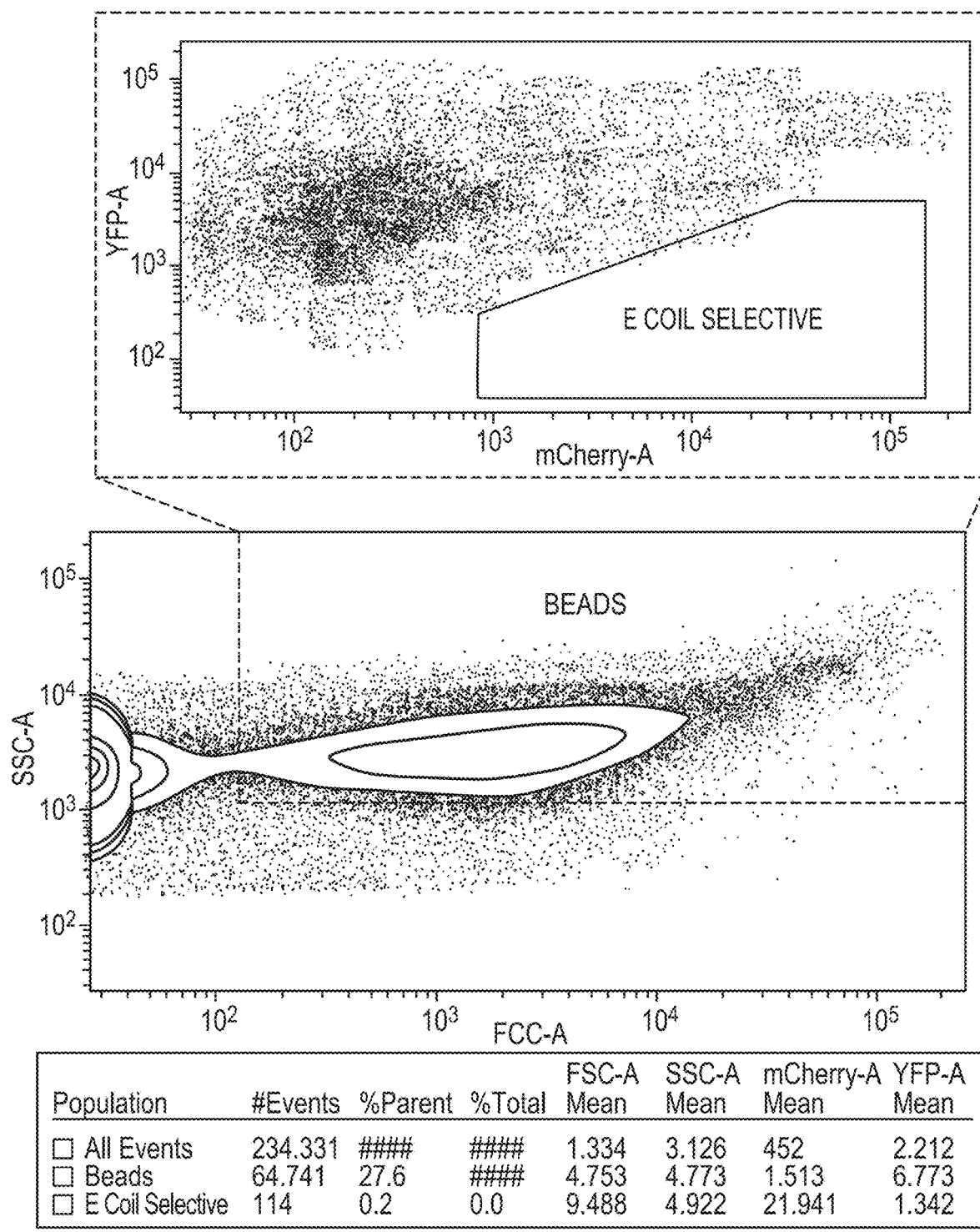
FIGS. 4A-4C illustrate representative high-throughput screening of microdroplets for identifying producer microorganisms having activity inhibiting Gram-negative bacteria.
Figures 1, 4B:
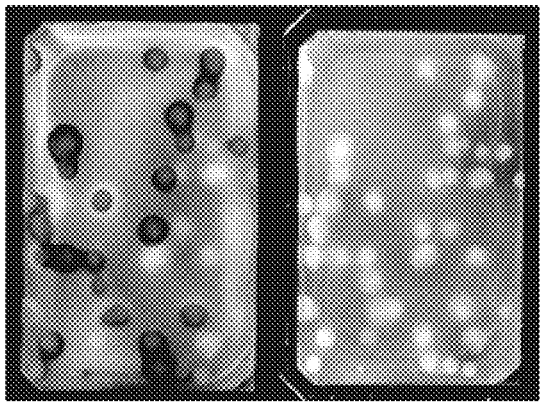
Figures 2, 4B:
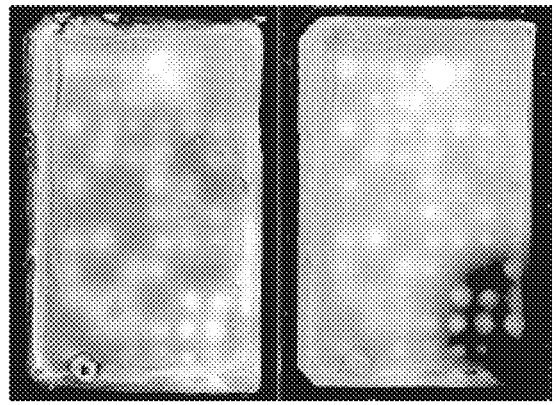
Figures 1, 4C:
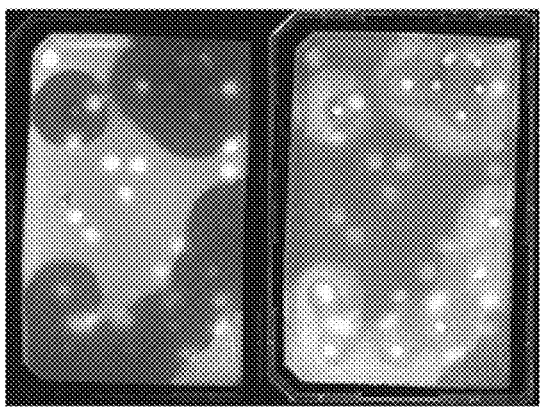
Figures 2, 4C:
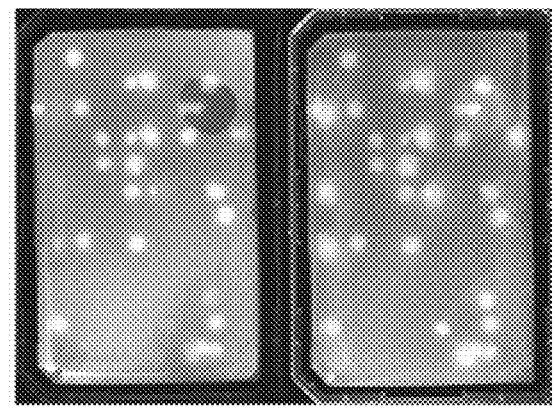

FIGS. 4A-4C illustrate representative high-throughput screening of microdroplets utilizing agarose beads for identifying producer microorganisms having activity inhibiting Gram-negative bacteria (e.g., *E. coli*). In various embodiments, *E. coli* is modified to express a yellow fluorescent protein (YFP) and Gram-positive bacteria (e.g., *Bacillus subtilis* or *S. aureus*) are modified to express a red fluorescent protein (e.g. mCherry). Agarose beads containing the potential producer microorganisms and a mixture of YFP-tagged *E. coli* and mCherry-tagged *B. subtilis* are then sorted by flow cytometry. For example, referring to FIG. 4A-1, the agarose beads are identified using forward and side scatter gating. As depicted in FIG. 4A-2, a fluorescence profile (e.g., YFP v.s. mCherry intensity) can be simultaneously interrogated for each bead and is used for sorting. A region ("*E. coli* selective") 402 in the profile that shows beads having low YFP signal (*E. coli*) and high mCherry signal (*B. subtilis*) corresponding to a putative co-encapsulated producer microorganism with selective inhibitory activity against *E. coli*, but not *B. subtilis* (0.2% sub-population) can be identified. Beads in the region 402 are then sorted onto nutrient agar plates and incubated to allow for growth of the producer microorganism.

In various embodiments, activity of the putative producer isolates on the agar plates is interrogated using approaches described in FIG. 1. For example, the reporter strains (e.g. YFP-tagged *E. coli* and mCherry-tagged *B. subtilis*) may be mixed and poured on the agar plate having colonies of putative producer isolates. After a 24-hour incubation, the agar plate is imaged using a suitable instrument (as described in FIG. 1) that excites at wavelengths appropriate to YFP and mCherry. FIG. 4B-1 illustrates representative results: unknown environmental producer microorganisms (obtained from soil) inhibit growth of YFP-tagged *E. coli* (dark regions in left panel) but not mCherry-tagged *B. subtilis* (right panel). FIG. 4B-2 depicts results of a control experiment where the agarose beads are randomly sorted onto the agar plates. As shown, growth of neither the YFP-tagged *E. coli* nor mCherry-tagged *B. subtilis* is significantly inhibited (with the exception of one Gram positive selective zone of inhibition, lower right corner of mCherry channel image). Accordingly, approaches described herein may efficiently detect selective activity of a compound or a producer thereof against a microorganism.

FIGS. 4C-1 and 4C-2 depict a control experiment where a known producer of the Gram-negative specific antimicrobial polymyxin is used. As shown, agar plates having beads corresponding to low YFP signal (*E. coli*) and high mCherry signal (*B. subtilis*) significantly inhibit growth of YFP-tagged *E. coli* (dark regions in left panel of FIG. 4C-1), but not mCherry-tagged *B. subtilis*.

Another variation of the method allows for identification of compounds that target mammalian cells, but not bacteria. In this embodiment, a transformed, adherent mammalian cell line such as HEK293 or HeLa expressing a fluorescent protein is seeded onto tissue culture-treated dishes and overlaid with the appropriate media supplemented with sterile, ultra low-melt agarose to create a barrier preventing direct contact between the mammalian cells and producer cells. The representative bacteria, fluorescently labeled *S. aureus*, is plated on top of the agarose layer. Separately, putative producer cells from environmental sources are cultivated in agar for the desired length of time. Agar slabs containing putative producer colonies are transferred to the agarose layer encapsulating the mammalian cells and allowed to incubate overnight. A zone surrounding a colony producing a compound acting against mammalian cells is revealed by a color corresponding to fluorescently labeled *S. aureus*, and absence of the color corresponding to fluorescently labeled mammalian cells. In other variations, such as in screens to identify compounds that modulate specific signaling pathways of interest, expression of the fluorescent protein may be placed under the control of an inducible enhancer (i.e. a caspase reporter to identify inducers of apoptosis or an NF-kB responsive reporter to enable identification of inflammatory modulators).

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A method of identifying a producer microorganism that makes a compound having selective inhibitory activity against a target microorganism, the method comprising the steps of:
    suspending first and second microorganisms in a nutrient medium, wherein (i) the first and second microorganisms are different from each other, (ii) the first microorganism exhibits a first detectable label, (iii) the second microorganism exhibits a second detectable label different from the first detectable label, (iv) neither of the labels interferes with detection of the other label, and (v) the second microorganism is the target microorganism;
    contacting the first and second microorganisms with a producer microorganism, that makes the compound, to produce a mixed culture;
    incubating the mixed culture;
    isolating a volume of the nutrient medium exhibiting the first label but not the second label; and
    identifying the producer of the compound having selective inhibitory activity against the target microorganism from said volume.

2. The method of claim 1, wherein the first and second detectable labels are fluorescent emissions having different peak wavelengths.

3. The method of claim 2, wherein the first and second microorganisms have been genetically modified to express fluorescent proteins emitting the labels.

4. The method of claim 3, wherein both of the peak wavelengths are in the visible spectrum.

5. The method of claim 4, wherein one of the wavelengths is green and one of the wavelengths is red.

6. The method of claim 1, wherein the first microorganism is gram positive and the second microorganism is gram negative.

7. The method of claim 1, wherein the first microorganism is gram positive and the second microorganism is a spirochete.

8. The method of claim 1, wherein the first microorganism is gram positive and the second microorganism is a fungus.

9. The method of claim 1, wherein the first microorganism is found in human gut flora and the second microorganism is a disease-causing pathogen.

10. The method of claim 1, wherein the first microorganism is found as a natural inhabitant of the human nasopharynx and the second microorganism is a disease-causing pathogen.

11. The method of claim 1, wherein the first microorganism is found as a natural inhabitant of the human oral cavity and the second microorganism is a disease-causing pathogen.

12. The method of claim 1, wherein the first microorganism is found as a natural inhabitant of the human vaginal microbiota and the second microorganism is a disease-causing pathogen.

13. The method of claim 1, wherein the first microorganism is found as a natural inhabitant of the human skin microbiome and the second microorganism is a disease-causing pathogen.

14. The method of claim 1, wherein the first microorganism is a bacterial or fungal cell and the second microorganism is a mammalian cell.

15. The method of claim 1, wherein the contacting and isolating steps further comprise:
mixing the producer of the compound with agar to produce a first mixture and spreading the mixture over a plate;
spreading the nutrient medium comprising the first and second microorganisms over the first mixture;
detecting at least one region of the plate where the first label is present and the second label is not present; and
isolating the producer of the compound from the at least one detected region.

16. The method of claim 15, wherein the producer of the compound is in a soil sample.

17. The method of claim 1, wherein the contacting and isolating steps further comprise:
mixing the producer of the compound with agar to produce a mixture and adding the nutrient medium comprising the first and second microorganisms to the mixture;
generating microdroplets from the mixture;
identifying microdroplets exhibiting the first label but not the second label; and
isolating the producer of the compound from the isolated microdroplets.

18. The method of claim 17, wherein the microdroplets include approximately equal numbers of the first and second microorganisms.

19. The method of claim 17, wherein the first and second detectable labels are fluorescent emissions having different peak wavelengths and the identifying step is performed using a fluorescence-activated cell sorter.

20. The method of claim 1, wherein the contacting and isolating steps further comprise:
mixing the producer of the compound with agarose beads and the nutrient medium comprising the first and second microorganisms;
identifying the agarose beads using forward and side scatter gating;
sorting agarose beads exhibiting the first label but not the second label; and
isolating the producer of the compound from the identified agarose beads.

* * * * *